(12) United States Patent
Trinh

(10) Patent No.: US 12,138,414 B2
(45) Date of Patent: Nov. 12, 2024

(54) MASK ASSEMBLY FOR FACE

(71) Applicant: ICY BEAUTY INC., Anaheim, CA (US)

(72) Inventor: Nancy Trinh, Anaheim, CA (US)

(73) Assignee: ICY Beauty Inc., Anaheim, CA (US)

(*) Notice: Subject to any disclaimer, the term of this patent is extended or adjusted under 35 U.S.C. 154(b) by 836 days.

(21) Appl. No.: 17/171,263

(22) Filed: Feb. 9, 2021

(65) Prior Publication Data

US 2021/0244924 A1    Aug. 12, 2021

Related U.S. Application Data

(60) Provisional application No. 62/972,513, filed on Feb. 10, 2020.

(51) Int. Cl.
| | |
|---|---|
| *A61M 35/00* | (2006.01) |
| *A61K 8/02* | (2006.01) |
| *A61K 8/34* | (2006.01) |
| *A61K 8/73* | (2006.01) |
| *A61K 8/81* | (2006.01) |
| *A61K 9/00* | (2006.01) |

(Continued)

(52) U.S. Cl.
CPC .......... *A61M 35/10* (2019.05); *A61K 8/0212* (2013.01); *A61K 8/345* (2013.01); *A61K 8/735* (2013.01); *A61K 8/8176* (2013.01); *A61K 9/0014* (2013.01); *A61K 9/7092* (2013.01); *A61K 31/05* (2013.01); *A61K 31/355* (2013.01); *A61K 31/375* (2013.01); *A61K 31/7048* (2013.01); *A61K 33/00* (2013.01); *A61K 33/06* (2013.01); *A61K 36/185* (2013.01); *A61K 36/28* (2013.01); *A61K 36/539* (2013.01); *A61K 38/4873* (2013.01); *A61Q 19/007* (2013.01); *A61M 2205/0205* (2013.01); *A61M 2205/3606* (2013.01); *A61M 2210/0625* (2013.01)

(58) Field of Classification Search
CPC .. A61K 8/0212; A61K 9/7092; A45D 44/002; A45D 44/22; A61Q 19/001; A61Q 19/00; A61F 2007/0003; A61F 2007/0017; A61M 35/10; A61M 25/0043; A61M 25/0045; A61M 2025/0048; A61M 2025/0047

See application file for complete search history.

(56) References Cited

U.S. PATENT DOCUMENTS

| | | |
|---|---|---|
| 2,434,078 A | 1/1948 | Malerman |
| 3,780,537 A | 12/1973 | Spencer |

(Continued)

FOREIGN PATENT DOCUMENTS

| | | | | |
|---|---|---|---|---|
| KR | 200486917 Y1 | * | 4/2017 | .......... A61K 8/0212 |
| WO | WO-2014140663 A1 | * | 9/2014 | .......... A45D 44/002 |

*Primary Examiner* — Leslie A Lopez
*Assistant Examiner* — Seth Han
(74) *Attorney, Agent, or Firm* — Knobbe, Martens, Olson & Bear, LLP

(57) ABSTRACT

A face mask or body cover assembly, including for lips, can include a band and a lip-contacting portion comprising a plurality of plastic liners, a skin healing formulation, and an ice pack gel solution filling. The face mask assembly can self-adhere to a patient's face. The skin healing formulation can include a first active botanical compound and a second active botanical compound that can function as an analgesic, an antimicrobial, an activity, an anti-inflammatory and/or an antioxidant.

16 Claims, 5 Drawing Sheets

(51) Int. Cl.
*A61K 9/70* (2006.01)
*A61K 31/05* (2006.01)
*A61K 31/355* (2006.01)
*A61K 31/375* (2006.01)
*A61K 31/7048* (2006.01)
*A61K 33/00* (2006.01)
*A61K 33/06* (2006.01)
*A61K 36/185* (2006.01)
*A61K 36/28* (2006.01)
*A61K 36/539* (2006.01)
*A61K 38/48* (2006.01)
*A61Q 19/00* (2006.01)

(56) References Cited

U.S. PATENT DOCUMENTS

| | | |
|---|---|---|
| 4,040,127 A | 8/1977 | Slovitt et al. |
| 4,393,975 A | 7/1983 | Moore |
| 4,527,565 A | 7/1985 | Ellis |
| 4,854,319 A | 8/1989 | Tobin |
| 4,953,550 A | 9/1990 | Dunshee |
| 4,983,122 A | 6/1991 | Mitnick |
| 5,119,812 A | 6/1992 | Angelo |
| 5,190,033 A | 3/1993 | Johnson |
| 5,356,426 A | 10/1994 | Delk et al. |
| 5,409,500 A | 4/1995 | Dyrek |
| 5,717,993 A | 2/1998 | Roberts |
| 6,099,555 A | 8/2000 | Sabin |
| 6,217,606 B1 | 4/2001 | Portnoy et al. |
| 6,241,711 B1 | 6/2001 | Weissberg et al. |
| 6,319,510 B1 | 11/2001 | Yates |
| 7,065,983 B2 | 6/2006 | Trinh et al. |
| 7,614,399 B2 | 11/2009 | Carstens |
| 8,596,273 B2 | 12/2013 | Burz et al. |
| 8,846,725 B2 | 9/2014 | Johnson et al. |
| 9,427,621 B2 | 8/2016 | Dristle |
| 9,511,016 B2 | 12/2016 | Oronsky et al. |
| 9,867,874 B1* | 1/2018 | VanderVeer ............ A61K 8/27 |
| 10,085,935 B2 | 10/2018 | Chen et al. |
| 10,314,737 B2 | 6/2019 | Loeffler |
| 2004/0138729 A1 | 7/2004 | Ladmer |
| 2005/0222654 A1 | 10/2005 | Brown |
| 2007/0023048 A1 | 2/2007 | Cho |
| 2007/0026028 A1* | 2/2007 | Close ................ B32B 5/22 |
| | | 2/167 |
| 2008/0141683 A1 | 6/2008 | O'Connor et al. |
| 2008/0161892 A1 | 7/2008 | Mercuro et al. |
| 2009/0062754 A1* | 3/2009 | Tang ............ A61F 13/02 |
| | | 604/307 |
| 2009/0130048 A1 | 5/2009 | Oronsky et al. |
| 2010/0071690 A1 | 3/2010 | Matich |
| 2013/0116762 A1 | 5/2013 | Lai |
| 2013/0152944 A1* | 6/2013 | Okada ................ A61F 13/024 |
| | | 606/204.15 |
| 2016/0051402 A1 | 2/2016 | Laghi et al. |
| 2016/0165992 A1 | 6/2016 | Brandt et al. |
| 2017/0014264 A1 | 1/2017 | Bradley et al. |
| 2018/0049913 A1 | 2/2018 | Spears et al. |
| 2018/0236129 A1 | 8/2018 | Roca Martinez et al. |

* cited by examiner

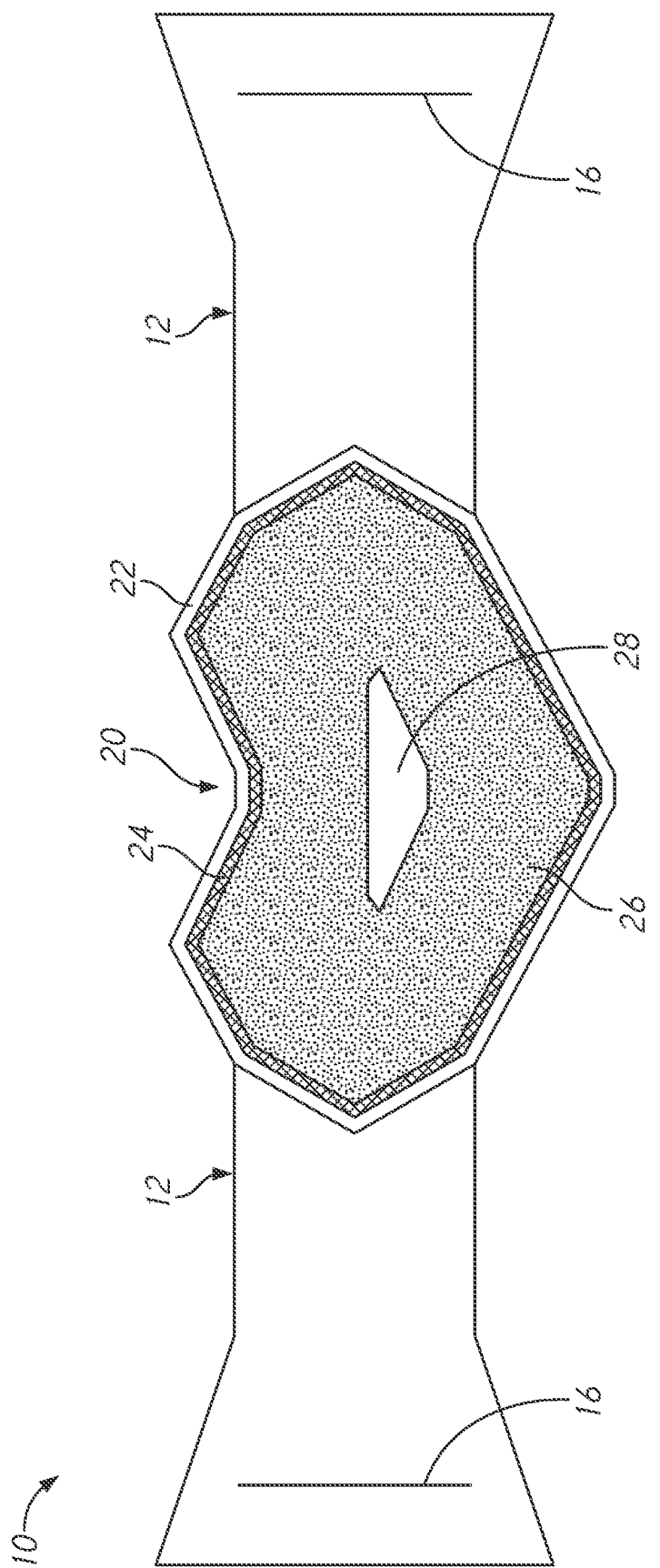

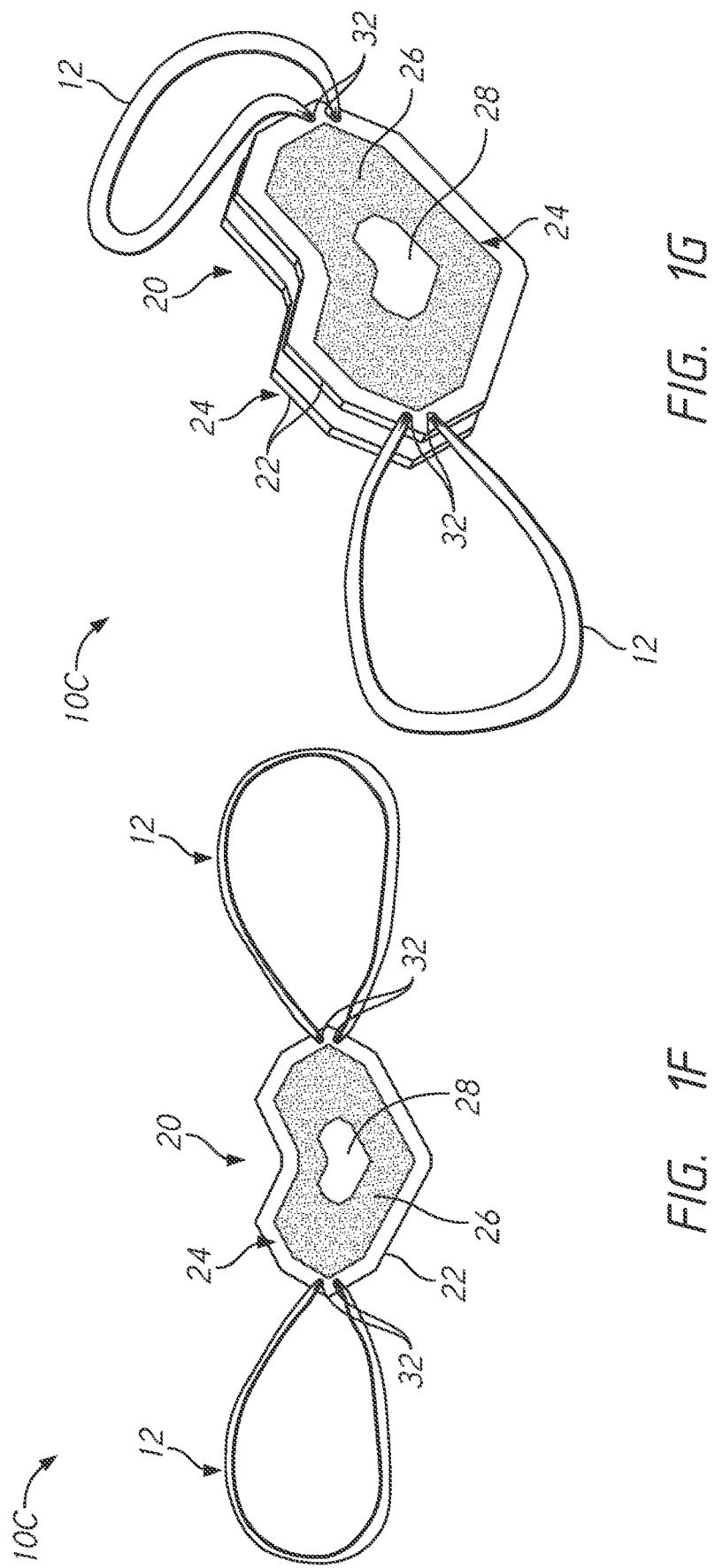

MASK ASSEMBLY FOR FACE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57. For example, the present application claims priority to U.S. Provisional Patent Application No. 62/972,513, filed Feb. 10, 2020.

BACKGROUND

Field

The present disclosure relates generally to mask assemblies, and in particular to face masks for use on, for example, lips.

Description of the Related Art

Patients often swell and bruise after being injected with cosmetic lip fillers or other cosmetic procedures, including to the face. Patients are often advised to ice their lips or other parts of the face, apply an *Arnica* topical to their lips, and/or to take Bromelain to reduce swelling and/or inflammation near the injection site.

Some medical offices do not offer ice packs to patients after lip filler procedures or other cosmetic procedures, including to the face. Some patients are sent home from medical offices without an ice pack, resulting in time spent on the drive home without having an ice pack on, for example, the patient's lip, thereby increasing the healing time of the patient. If a patient is given an ice pack after the lip filler treatment, the patient generally holds the ice pack in one hand and drives with the other hand, alternating hands intermittently, which can be dangerous. The patient is unable to simultaneously apply an ice pack to his or her lips (or other parts of the face) and operate a vehicle hands-free. Holding an ice pack up to the patient's lips or other parts of the face can also become messy as the ice melts and moisture collects on the exterior of the ice pack.

Furthermore, the patient generally needs to purchase a topical analgesic ointment and apply the topical analgesic to the lip, separately from icing the lip, to keep the lip moisturized and help it heal.

SUMMARY

A hybrid sheet mask and ice gel pack can help patients who receive lip filler treatment(s) or other cosmetic procedures, including to the face, heal faster. In some embodiments, the lip mask assembly can include a hands-free ice pack and a topical analgesic. A self-adhered frozen lip mask assembly or other face mask assembly can allow a patient to drive home safely from a medical office, with both of the patient's hands being free to operate a vehicle. In some embodiments, the lip mask assembly can deposit a particular amount of topical analgesic on the patient's lips. The topical ointment can be made of natural ingredients that can help the patient heal faster.

In some embodiments, a lip mask assembly comprises a support band, a lip-contacting portion, and a skin healing formulation. The lip mask assembly can be configured for placement over lips of a user to facilitate skin healing of the user. The support band can comprise a first portion and a second portion. Each of the first and second portions of the support band can be configured to receive an ear of a user. The lip-contacting portion can be configured to contact lips of the user. The lip-contacting portion can be attached to the support band. The lip-contacting portion can be positioned between the first and second portions of the support band. The lip-contacting portion can comprise a first liner, a second liner, and a gel solution filling. The first liner can have an outwardly facing surface and an inwardly facing surface. The second liner can have an outwardly facing surface and an inwardly facing surface. The inwardly facing surface of the second liner can be positioned to face the inwardly facing surface of the first liner. The gel solution filling can be disposed between the inwardly facing surface of the first liner and the inwardly facing surface of the second liner. The gel solution filling can be configured to be cooled relative to ambient temperature. The skin healing formulation can be disposed on the outwardly facing surface of at least one of the first liner or the second liner. The skin healing formulation can comprise at least a first active botanical compound and at least a second active botanical compound.

The skin healing formulation can be disposed on the outwardly facing surface of the first liner and the outwardly facing surface of the second liner. The lip mask assembly can further comprise a first protective cover configured to removably cover the skin healing formulation disposed on the outwardly facing surface of the first liner. The first protective cover can be configured to be removed to expose the skin healing formulation.

The lip mask assembly can further comprise a second protective cover configured to removably cover the skin healing formulation disposed on the outwardly facing surface of the second liner. The second protective cover can be configured to be removed to expose the skin healing formulation.

The lip mask assembly can further comprise a seal between the first and second liners. The seal can be configured to prevent leakage of the gel solution filling from the lip-contacting portion. The lip mask assembly can further comprise adhesive attaching the lip-contacting portion to the first and second portions of the support band.

The lip-contacting portion can further comprise an opening for the user's mouth. The opening can extend through the first and second liners. The lip-contacting portion can be configured to extend over the user's mouth.

The lip mask assembly can comprise adhesive configured to support the lip mask assembly on the user's face.

The gel solution filling can be configured to be frozen.

The first and second portions of the support band can be ear straps. The lip mask assembly can further comprise a plurality of apertures disposed near the perimeter of the lip-contacting portion. Each of the plurality of apertures can be configured to receive a portion of one of the ear straps.

The support band can comprise a stretchy fabric. Each of the first and second portions of the support band can comprise a slit for receiving one of the user's ears.

The first active botanical compound can be configured to provide analgesic activity. The first active botanical compound can be configured to provide antimicrobial activity. The first active botanical compound can be configured to provide anti-inflammatory activity. The first active botanical compound can be configured to provide antioxidant activity. The first active botanical compound can be an *Arnica montana* extract.

The second active botanical compound can be configured to provide analgesic activity. The second active botanical compound can be configured to provide antimicrobial activity. The second active botanical compound can be configured to provide anti-inflammatory activity.

The second active botanical compound can be selected from the group consisting of bromelain, *Calendula officials* flower extract, *Cannabis sativa* seed extract, cannabidiol, *Scutellaria baicalensis* root extract, tocopherol, tocopheryl acetate, ascorbic acid, magnesium ascorbyl phosphate, sodium ascorbyl phosphate, ascorbyl glucoside, tetrahexyldecyl ascorbate, and 3-o-ethyl ascorbic acid.

The second active botanical compound can be bromelain.

The skin healing formulation can further comprise *Calendula officials* flower extract, *Cannabis sativa* seed extract, cannibidiol, or combinations of any of the foregoing.

The skin healing formulation can further comprise *Scutellaria baicalensis* root extract, tocopherol, tocopheryl acetate, ascorbic acid, magnesium ascorbyl phosphate, sodium ascorbyl phosphate, ascorbyl glucoside, tetrahexyldecyl ascorbate, 3-o-ethyl ascorbic acid, or combinations of any of the foregoing.

The skin healing formulation can comprise a skin moisturizer, wherein the skin moisturizer comprises hyaluronic acid, a glycol, glycerin, sodium pyrrolidone carboxylic acid, or combinations of any of the foregoing.

Methods of using the system(s) (including device(s), apparatus(es), assembly(ies), structure(s), and/or the like) disclosed herein are included; the methods of use can include using or assembling any one or more of the features disclosed herein to achieve functions and/or features of the system(s) as discussed in this disclosure. Methods of manufacturing the system(s) disclosed herein are included; the methods of manufacture can include providing, making, connecting, assembling, and/or installing any one or more of the features of the system(s) disclosed herein to achieve functions and/or features of the system(s) as discussed in this disclosure. An example method of use is as follows.

In some embodiments, a method of using a lip mask assembly comprises removing a first protective cover, applying the lip mask assembly to a user's face, and sliding a support band over the user's ear. Removing the first protective cover from a surface of a first liner of a lip-contacting portion of a lip mask assembly can expose a skin healing formulation disposed on the surface of the first liner. The skin healing formulation can comprise at least a first active botanical compound and at least a second active botanical compound. Applying the lip mask assembly to the user's face can cause the skin healing formulation disposed on the surface of the first liner to contact skin of the user. Sliding the support band over the user's ear can help to secure the lip mask assembly to the user's face.

The method can further comprise removing a second protective cover from a surface of a second liner of the lip-contacting portion of the lip mask assembly. Removing the second protective cover from the surface of the second liner can expose additional skin healing formulation disposed on the surface of the second liner.

The method can further comprise applying the lip mask assembly to the user's face such that the additional skin healing formulation disposed on the surface of the second liner contacts skin of the user.

The method can further comprise cooling a gel solution filling in contact with the first liner to a temperature below ambient temperature. This can provide cooling to skin of the user after applying the lip mask assembly to the user's face.

In some embodiments, a body cover assembly for placement over skin of a user to facilitate skin healing of the user comprises a skin-contacting cover and a skin healing formulation. The skin-contacting cover can be configured to contact skin of the user. The skin-contacting cover can comprise a first liner having a first surface and a second surface. The skin healing formulation can be positioned on the first surface of the first liner. The skin healing formulation can comprise at least a first active botanical compound and at least a second active botanical compound.

The body cover assembly can further comprise a protective cover on the first surface. The protective cover can be positioned over the skin healing formulation on the first surface of the first liner. The protective cover can be configured to be removed to expose the skin healing formulation.

The body cover can further comprise a gel solution filling positioned on the second surface of the first liner. The gel solution filling can be configured to be cooled relative to ambient temperature.

The skin-contacting cover can comprise a second liner with gel solution filling positioned on both the first and second liners such that the gel solution filling is positioned between the first and second liners of the skin-contacting cover.

This Summary is provided to introduce a selection of concepts in a simplified form that are further described below in the Detailed Description. This Summary is not intended to identify key features or essential features of any subject matter described herein.

BRIEF DESCRIPTION OF THE DRAWINGS

The features of the lip mask assemblies disclosed herein are described below with reference to the drawings of certain embodiments. The illustrated embodiments are intended to demonstrate, but not to limit, the present disclosure. The proportions and relative dimensions and sizes of each component as shown in these drawings form part of the supporting disclosure of this specification, but should not be limiting on the scope of this specification, except to the extent that such proportions, dimensions, or sizes are included in any individual claims. The drawings contain the following Figures:

FIG. 1A is a schematic illustrating a front view of an embodiment of a lip mask assembly.

FIGS. 1F and 1G are schematics illustrating front and perspective views, respectively, of another embodiment of a lip mask assembly.

DETAILED DESCRIPTION OF CERTAIN EMBODIMENTS

Figure 1C:
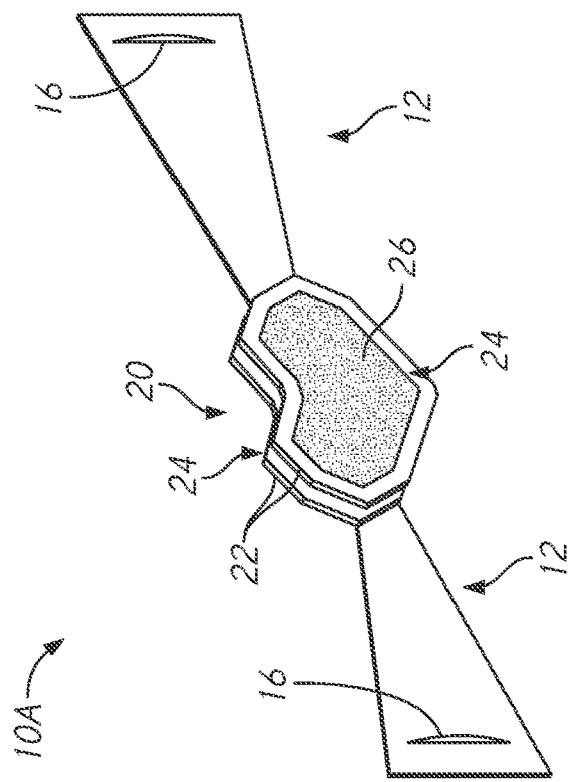
FIGS. 1B and 1C are schematics illustrating front and perspective views, respectively, of another embodiment of a lip mask assembly.

Certain embodiments of an assembly for reducing a patient's swelling are disclosed in the context of a lip mask, as it has particular utility in this context. However, various aspects of the present disclosure can be used in many other contexts as well such as other parts of the face or in combination with other parts of the face and lips. Various aspects of the present disclosure can also be used on other body parts to reduce swelling and pain. Further, while the assemblies, devices, systems, and methods herein are described in the context of cosmetic procedures, the assemblies, devices, system, and methods may also be used after other medical procedures such as surgery or other non-medical applications such as after sports injuries or strains. None of the features described herein are essential or indispensable. Any feature, structure, or step disclosed herein can be replaced with or combined with any other feature, structure, or step disclosed herein, or omitted.

As used herein, the term "weight percent," when referring to a component, is the weight of the component divided by the weight of the composition that includes the component, multiplied by 100%. For example the weight percent of component A when 5 grams of component A is added to 95 grams of component B is 5% (e.g., 5 g A/(5 g A+95 g B)×100%).

As used herein, when the term "collectively or individually" (and variations thereof) modifies an amount of a component or components (e.g., a weight percent) of multiple component composition, this usage means that each individual component may be provided in the amount disclosed or that combined amount of components may be provided in the amount disclosed. For example, if agents A and B are referred to as, collectively or individually, being present in a composition at a wt % of 5%, that means that A may be at 5 wt % in the composition (individually), B may be at 5 wt % in the composition (individually), or the combination of A and B may be present at a total of 5 wt % (A+B=5 wt %, e.g., collectively). Where A is present at 5 wt %, B may be absent. Where B is present at 5 wt %, A may be absent. Alternatively, where both A and B are present, A may be at 5 wt % (individually) and B may be at 5 wt % (individually), totaling 10 wt % (collectively).

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including." "containing." or "characterized by." and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably." "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Additionally, the phrase "consisting essentially of" will be understood to include those elements specifically recited and those additional elements that do not materially affect the basic and novel characteristics of the claimed technology. The phrase "consisting of" excludes any element not specified.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

In some embodiments, the mask assembly 10 can comprise a hybrid sheet mask and ice gel pack (or other cooling formulations). The lip mask assembly 10 can help reduce swelling and/or bruising of a patient and help the patient heal faster after receiving a lip filler treatment. The lip mask assembly 10 can be used conveniently and with minimal effort, allowing the patient to wear the lip mask assembly 10 and engage in other activities, such as driving, with each of the patient's hands available.

The mask assembly 10 can provide a hands-free way to attach an ice pack to a patient's face and/or to apply a custom formulation of healing ingredients to the patient's lips. For example, the mask assembly 10 can self-adhere to the patient's face. The lip-contacting or face-contacting portion 20 can include a composition 24 (e.g., a custom skin healing formulation) and/or a gel solution filling 26. In several embodiments, the composition 24 may include one or more active ingredients. In several embodiments, as disclose elsewhere herein, an active ingredient may include a compound configured to provide analgesic activity (e.g., an analgesic compound), antimicrobial activity (e.g., an anti-microbial compound), anti-inflammatory activity (e.g., an antimicrobial compound), and/or antioxidant activity (e.g., an anti-oxidant). In several embodiments, multiple active ingredients may be provided in the skin healing formulation.

As shown in FIGS. 1A-1G, in some embodiments, a lip mask or face mask assembly 10, 10A, 10B, 10C includes a lip-contacting or face-contacting portion (or cover) 20 and a band 12 (e.g., a support band). The band 12 can be attached to the lip-contacting portion 20 (e.g., using adhesive such as glue, by extending portions of the band 12 through openings in the lip-contacting portion 20, by sewing the band 12 to the lip-contacting portion 20, etc.). The band 12 can comprise a first portion and a second portion. The lip-contacting portion 20 can be positioned laterally between the first portion and the second portion of the band 12 (FIGS. 1A-1G). A first side of the lip-contacting portion 20 can be connected to the first portion of the band 12 and a second side of the lip-contacting portion 20, opposite the first side, can be connected to the second portion of the band 12.

Figure 1B:
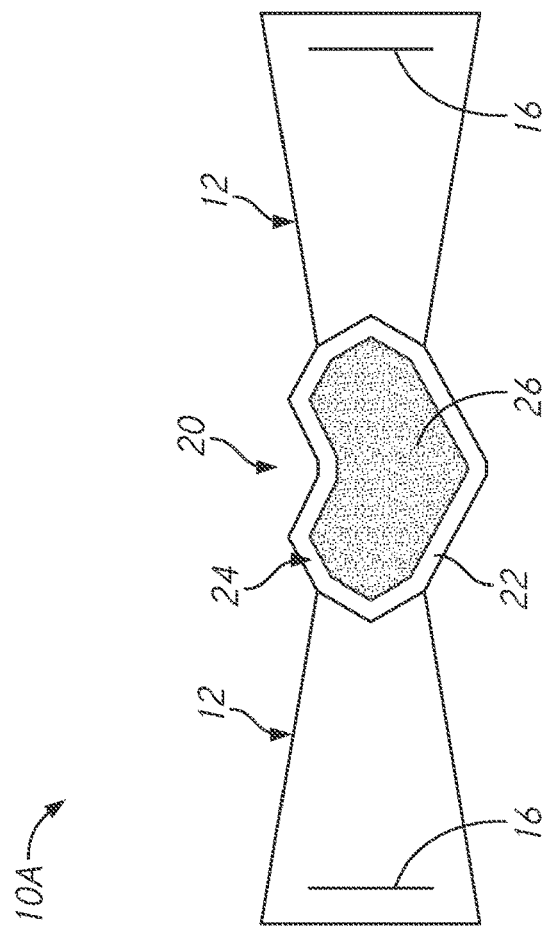
Figure 1E:
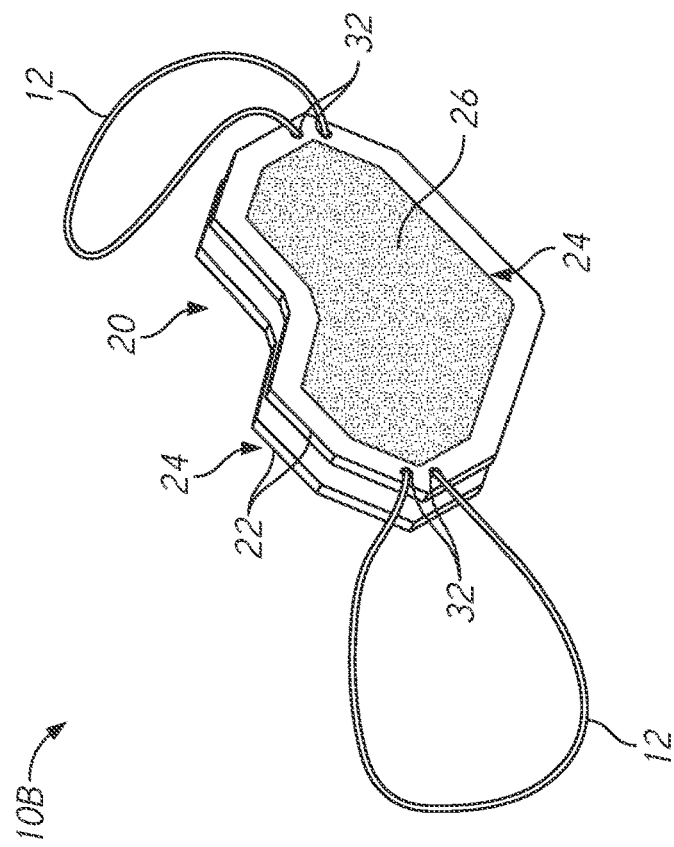
FIGS. 1D and 1E are schematics illustrating front and perspective views, respectively, of another embodiment of a lip mask assembly.
Figure 1D:
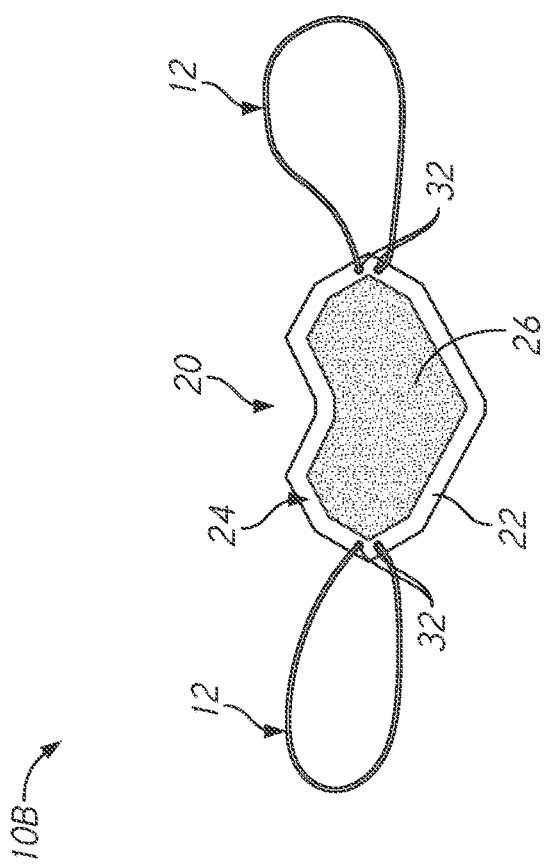

The band 12 can comprise a stretchy, soft fabric (natural and/or synthetic). In some embodiments, the band 12 can include slits 16 in each of the first and second portions, the slits 16 configured to go over and/or around a patient's ears (FIGS. 1A, 1B, 1C). The band 12 can help support the weight of the lip-contacting portion 20. This can advantageously help secure the lip mask assembly 10 in a particular position on the patient's face.

In some embodiments, the width of the band 12 varies (e.g., tapers) along the length of the band 12. For example, each of the first and second portions of the band 12 can be narrower closer to the lip-contacting portion 20 and wider further from the lip-contacting portion 20 (e.g., closer to where the band 12 receives the user's ears) (FIGS. 1A-1C).

In some embodiments, the first and second portions of the band 12 are ear straps or ear loops (e.g., thin elastic bands for placing over the user's ears) (FIGS. 1D-1G). In some embodiments, the first and second portions of the band 12 can be knotted 80% Nylon, 20% elastic bands for placing over the user's ears (FIGS. 1F-1G).

In some embodiments, the lip-contacting portion 20 comprises a plurality of apertures 32 (e.g., two apertures, three apertures, etc.) for attaching the first and second portions of the band 12 to the lip-contacting portion 20 (FIGS. 1D-1G). Each of the apertures 32 can be configured to receive at least a segment of one of the first portion or the second portion of the band 12. One or more of the apertures 32 can be positioned towards the perimeter of the lip-contacting portion 20 (e.g., towards the edges of the forward facing surface of the lip-contacting portion 20). In some embodiments, two apertures 32 are positioned near or along the first side of the lip-contacting portion 20 and two apertures 32 are positioned near or along the second side of the lip-contacting portion 20 opposite the first side.

Figure 2B:
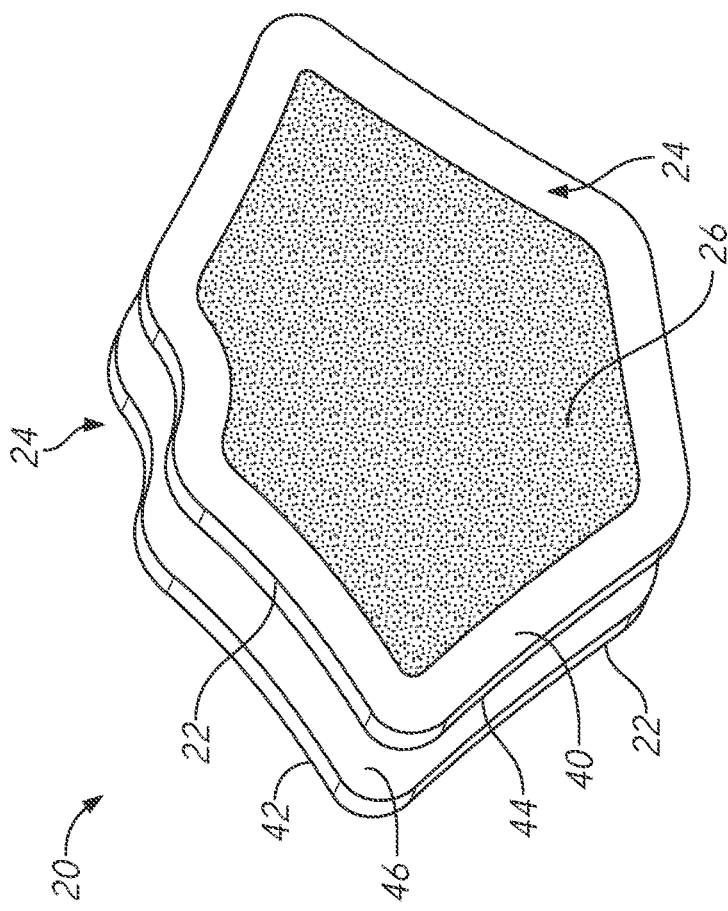
FIGS. 2A and 2B are schematics illustrating exploded views of embodiments of a lip-contacting portion of a lip mask assembly.
Figure 2A:
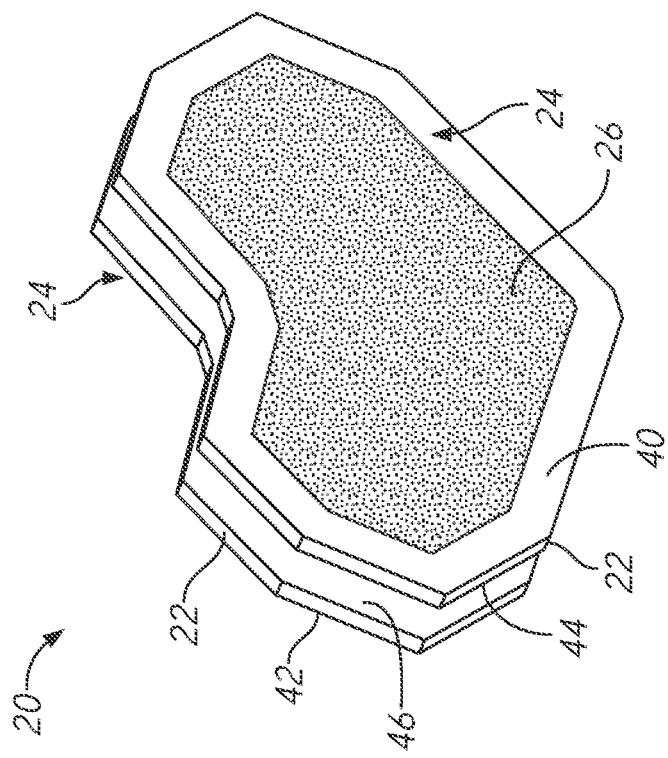

As illustrated in FIGS. 2A and 2B, the lip mask or face mask assembly 10 includes a lip-contacting or face-contacting portion 20 but does not include a band 12. For example, in some embodiments, the adhesive nature of the lip-contacting portion 20 is such that the lip-contacting portion 20 is configured to self-support itself on a user's face.

The lip-contacting or face-contacting portion 20 can comprise a plurality of layers. In some embodiments, one or more layers described herein may not be present or be removed from the mask assembly. In some embodiments, the lip-contacting portion 20 can comprise a plurality of liners 22, such as heat-sealed plastic liners, that can form or be part of the plurality of layers of the lip-contacting portion 20. For example, in some embodiments, as shown in FIGS. 2A and 2B, the lip-contacting portion 20 comprises a first liner 22 and a second liner 22. The first liner 22 can have an outwardly facing surface or first surface 40 and an inwardly facing surface or second surface 44 (FIGS. 2A, 2B). The second liner 22 can have an outwardly facing surface or first surface 42 and an inwardly facing surface or second surface 46 (FIGS. 2A, 2B). The inwardly facing surface 46 of the second liner 22 can be positioned to face the inwardly facing surface 44 of the first liner 22. The first and second liners 22 can be disposed on either side of the gel solution filling 26. In some embodiments, the first and second liners 22 can seal the gel solution filling 26 in between the liners 22 and prevent leakage of the gel solution filling 26. For example, the first and second liners 22 can be sealed together around their outer perimeters.

The gel solution filling 26 can comprise a gel solution filling 26 with properties similar to or the same as those of an ice pack gel solution filling. The gel solution filling 26 can be non-toxic. The gel solution filling 26 can be drain safe. The gel solution filling 26 can be configured to be cooled relative to ambient temperature (e.g., to a temperature below ambient temperature). For example, the gel solution filling 26 can be configured to be frozen. Cooling the gel solution filling 26 prior to application of the lip mask assembly 10 to the user's face (or between applications of the lip mask assembly 10 to the user's face) can advantageously aid in cooling the skin of the user when the lip mask assembly 10 is applied to the user's face. The gel solution filling 26 and/or liners 22 can be made of ice pack materials.

In some embodiments, the first and second liners 22 separate the gel solution filling 26 from the skin healing formulation 24. For example, in some embodiments, the skin healing formulation 24 is disposed on the outwardly facing surface 40 of the first liner 22 and/or the outwardly facing surface 42 of the second liner 22. Each side of the lip-contacting portion 20 can include a certain amount of the skin healing formulation 24. In some embodiments, each of the first and second liners 22 can be used for treatment. For example, during a first treatment, the user can use the first liner 22 or a first side of the lip-contacting portion 20 (including in some embodiments, in combination with the gel solution filling 26 that had been previously frozen or made cold). During a second treatment, the user can flip the lip mask assembly 10 and use the second liner 22 or the second side of the lip-contacting portion 20, opposite the first liner 22 or the first side of the lip-contacting portion 20 (including in some embodiments, in combination with the gel solution filling 26 that had been previously frozen or made cold, again).

In some embodiments, the skin healing formulation 24 is supported on or within a hydrogel. In several embodiments, the hydrogel comprises a polymer or copolymer comprising hydrophilic groups. In several embodiments, the hydrogel comprises one or more of the following polymers: polyvinyl alcohol, polyalkylene glycol, polyacrylate, polyacrylamide, or combinations of any of the foregoing. In several embodiments, the hydrogel comprises one or more of the following proteins: collagen, gelatin and fibrin, or combinations of any of the foregoing.

In several embodiments, the skin healing formulation 24 is supported on or within the gel (e.g., hydrogel). For example, the skin healing formation may be provided together as a blend formulation. In several embodiments, the blend formulation includes the skin healing formulation 24 and the gel (e.g., hydrogel). In several embodiments, the skin healing formulation 24 and the gel (e.g., hydrogel) are combined as a mixture in the blend formulation. In other embodiments, the skin healing formulation 24 and the gel (e.g., hydrogel) are separate components. For example, the skin healing formulation may be placed on a surface of the gel (e.g., hydrogel). When placed on the surface of the gel, the skin healing formulation may absorb into and/or integrate with the gel. In several embodiments, the skin healing formulation may adhere to the surface of the gel.

In several embodiments, the gel comprises water. Thus, the blend formulation may also comprise water. In several embodiments, water of the blend formulation is provided as a component of the hydrogel. In several embodiments, the water is present in the blend formulation (and/or in the gel) at a weight percent of equal to or greater than about: 20%, 40%, 60%, 65%, 70%, 75%, 80%, 85%, 90%, 95%, or ranges including and/or spanning the aforementioned values.

As disclosed elsewhere herein, in several embodiments, the skin healing formulation may include one or more active ingredients. In several embodiments, as disclosed elsewhere herein, an active ingredient may include a compound configured to provide analgesic activity (e.g., an analgesic compound), antimicrobial activity (e.g., an antimicrobial compound), anti-inflammatory activity (e.g., an antimicrobial compound), and/or antioxidant activity (e.g., an antioxidant). In several embodiments, the formulation comprises at least a first active ingredient. In several embodiment, the formulation further comprises a second active ingredient. In several embodiments, the formulation further comprises additional active ingredients (a third, fourth, fifth, sixth, etc.).

As disclosed elsewhere herein, in several embodiments, the formulation (e.g., skin healing formulation) comprises one or more analgesic compounds. In several embodiments, the analgesic compound is selected from the group consisting of clove extract, frankincense extract, *harpagophytum* extract, kratom extract, *Rhodiola rosea* extract, turmeric extract, willow bark extract, bromelain, *Arnica montana* flower extract, or combinations of any of the foregoing. In several embodiments, the analgesic compound is selected from the group consisting of berberine, boswellic acid, curcumin, eugenol, harpagoside, incensole acetate, mitragynine, 7-hydroxymitragynine, phellandrene, salicin, or combinations of any of the foregoing. In several embodiments, the analgesic compound is selected from the group consisting of *Arnica montana* flower extract, bromelain, or combinations thereof. In several embodiments, the analgesic (or analgesics), collectively or individually, are present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values. In several embodiments, the analgesic is *Arnica montana* flower extract. In several embodiments, the *Arnica montana* flower present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values. In several embodiments, the analgesic comprises *Arnica montana* flower extract and bromelain. In several embodiments, the bromelain present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values.

As disclosed elsewhere herein, in several embodiments, the formulation (e.g., skin healing formulation) comprises one or more antimicrobial compounds. In several embodiments, the antimicrobial compound is selected from the group consisting of cinnamon extract, clove extract, coriander extract, garlic extract, mustard extract, oregano extract, thyme extract, vanilla extract, bromelain, *Arnica montana* flower extract, or combinations of any of the foregoing. In several embodiments, the antimicrobial compound is selected from the group consisting of cinnamon oil, clove oil, coriander oil, garlic oil, mustard oil, oregano oil, thyme oil, vanilla oil, or combinations of any of the foregoing. In several embodiments, the antimicrobial compound is selected from the group consisting of flavonoids, glucosinolates, organic acids, phenols, saponins, thiosulfinates, or combinations of any of the foregoing. In several embodiments, the antimicrobial compound is selected from the group consisting of allicin, dihydroxybenzaldehyde, 2-hydroxy-5-methoxybenzaldehyde, trihydroxybenzaldehyde, 2,5-dihydroxybenzaldehyde, caffeic acid, carnosic acid, carnosol, carvacrol, cephalosporin, chlorogenic acid, 1,8-cincole, cinnamic aldehyde, cinnamic acid, methyl cinnamate, citral, p-cymene, eugenol, gallic acid, geraniol, β-lactam, linalool, penicillin, γ-terpinene, allyl isothiocyanate, thymol, vanillic acid, vanillin, or combinations of any of the foregoing. In several embodiments, the analgesic compound is selected from the group consisting of *Arnica montana* flower extract, bromelain, or combinations thereof. In several embodiments, the antimicrobial (or antimicrobials), collectively or individually, are present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values. In several embodiments, the antimicrobial is *Arnica montana* flower extract. In several embodiments, the *Arnica montana* flower present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values. In several embodiments, the antimicrobial comprises *Arnica montana* flower extract and bromelain. In several embodiments, the bromelain present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values.

As disclosed elsewhere herein, in several embodiments, the formulation (e.g., skin healing formulation) comprises one or more anti-inflammatory compounds. In several embodiments, the analgesic compound is selected from the group consisting of *Acacia catechu* extract, *Azadirachta indica* extract, *Caesalpinia crista* extract, *Cassia angustifolia* extract, *Coriandrum sativum* extract, *Cuscuta reflexa* extract, *Enicostema littorale* extract, *Erythrina variegate* extract, *Euphorbia hirta* extract, *Euphorbia tirucalli* extract, *Fagonia cretica* extract, *Ficus benghalensis* extract, *Ficus carica* extract, *Ficus religiosa* extract, *Foeniculum vulgare* extract, *Gentiana kuroo* extract, *Gloriosa superba* extract, *Glycyrrhiza glabra* extract, *Gmelina* arbórea extract, *Grewia asiatica* extract, *Hibiscus rosa-Sinensis* extract, *Hygrophila auriculata* extract, *Manihot esculenta* extract, *Martynia annua* extract, *Momordica charantia* extract, *Moringa oleifera* extract, *Nelumbo nucifera* extract, *Nicotiana tobacum* extract, *Nigella sativa* extract, *Ocimum basilicum* extract, *Plumbago zeylanica* extract, *Portulaca oleraceae* extract, *Pterocarpus marsupium* extract, *Solanum melongena* extract, *Solanum nigrum* extract, *Stereopermum suaveolens* extract, *Tephrosia purpurea* extract, *Terminalia chebula* extract, *Thespesia populnea* extract, *Thespesia populneoides* extract, *Tinospora cordifolia* extract, *Vernonia cinerea* extract, turmeric extract, *Calendula officials* extract, *Cannabis sativa* seed extract, a cannabinoid, bromelain, *Arnica montana* flower extract, or combinations of any of the foregoing. In several embodiments, the cannabinoid is selected from the group of tetrahydrocannabinolic acid (THCA), cannabidiolic acid (CBDA), cannabigerol (CBG), cannabichromene (CBC), cannabicyclol (CBL), cannabivarin (CBV), tetrahydrocannabiorcol (THCC), tetrahydrocannabivarin (THCV), tetrahydrocannabiphorol (THCP), cannabidivarin (CBDV), cannabichromevarin (CBCV), cannabigerovarin (CBGV), cannabigerol monomethyl ether (CBGM), cannabielsoin (CBE), cannabicitran (CBT), cannabinol (CBN), cannabidiol (CBD), or combinations of any of the foregoing. In several embodiments, the anti-inflammatory is selected from the group consisting of *Calendula officials* extract, *Cannabis sativa* seed extract, cannabidiol, bromelain, *Arnica montana* flower extract, or combinations of any of the foregoing. In several embodiments, the anti-inflammatory compound (or anti-inflammatory compounds), collectively or individually, are present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values. In several embodiments, the anti-inflammatory is *Arnica montana* flower extract. In several embodiments, the *Arnica montana* flower extract is present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values. In several embodiments, the anti-inflammatory is *Arnica montana* flower extract, bromelain, *Calendula officials* extract, *Cannabis sativa* seed extract, cannabidiol, or combinations of any of the foregoing. In several embodiments, the bromelain is present in the skin healing formulation (or in the blend formulation) at a weight percent of equal to or less than about: 0.1%, 0.5%, 2%, 5%, 7.5%, 10%, 15%, 20%, 25%, or ranges including and/or spanning the aforementioned values. In several embodiments, the *Calendula officials* extract is present in the skin healing formulation (or in the blend formulation) at a weight percent of equal to or less than about: 0.1%, 0.5%, 2%, 5%, 7.5%, 10%, 15%, 20%, 25%, or ranges including and/or spanning the aforementioned values. In several embodiments, the *Cannabis sativa* seed extract is present in the skin healing formulation (or in the blend formulation) at a weight percent of equal to or less than about: 0.1%, 0.5%, 2%, 5%, 7.5%, 10%, 15%, 20%, 25%, or ranges including and/or spanning the aforementioned values. In several embodiments, the cannabidiol is present in the skin healing formulation (or in the blend formulation) at a weight percent of equal to or less than about: 0.1%, 0.5%, 2%, 5%, 7.5%, 10%, 15%, 20%, 25%, or ranges including and/or spanning the aforementioned values.

As disclosed elsewhere herein, in several embodiments, the formulation (e.g., skin healing formulation) comprises one or more antioxidant compounds. In several embodiments, the antioxidant compound is selected from the group consisting of Aloe extract, herb extract, spice extract, fruit extract, grain extract, fungus extract, fruit waste extract, vegetable extract, legume extract, *Arnica montana* flower extract, or combinations of any of the foregoing. In several embodiments, the antioxidant compound is selected from the group consisting of oregano extract, cinnamon extract, clove extract, sage extract, turmeric extract, date extract, pomegranate extract, guava extract, persimmon extract, plum extract, grape extract, rice extract, buckwheat extract, fruit peel extract, fruit seed extract, beet extract, broccoli extract, Brussels sprout extract, cabbage extract, eggplant extract, pepper extract, bean extract, or combinations of any of the foregoing. In several embodiments, the antioxidant is selected from the group consisting of *Arnica montana* flower extract, *Scutellaria baicalensis* root extract, vitamin E (e.g., tocopherol or tocopheryl acetate), vitamin C (e.g., l-ascorbic acid, magnesium ascorbyl phosphate, sodium ascorbyl phosphate, ascorbyl glucoside, tetrahexyldecyl ascorbate, 3-o-ethyl ascorbic acid), or combinations of any of the foregoing. In several embodiments, the antioxidant compound (or antioxidant compounds), collectively or individually, are present in the formulation at a weight percent of equal to or less than about: 0.1%, 0.5%, 2%, 5%, 7.5%, 10%, 15%, 20%, 25%, or ranges including and/or spanning the aforementioned values. In several embodiments, the antioxidant is *Arnica montana* flower extract. In several embodiments, the *Arnica montana* flower extract is present in the formulation at a weight percent of equal to or less than about: 0.1%, 0.5%, 2%, 5%, 7.5%, 10%, 15%, 20%, 25%, 30%, 40%, 60%, or ranges including and/or spanning the aforementioned values. In several embodiments, the antioxidant is *Arnica montana* flower extract, *Scutellaria baicalensis* root extract, vitamin E (e.g., tocopherol or tocopheryl acetate), vitamin C (e.g., l-ascorbic acid, magnesium ascorbyl phosphate, sodium ascorbyl phosphate, ascorbyl glucoside, tetrahexyldecyl ascorbate, 3-o-ethyl ascorbic acid), or combinations of any of the foregoing. In several embodiments, the *Scutellaria baicalensis* root extract is present in the formulation at a weight percent of equal to or less than about: 0.1%, 0.5%, 2%, 5%, 7.5%, 10%, 15%, 20%, 25%, 30%, 40%, 60%, or ranges including and/or spanning the aforementioned values. In several embodiments, the vitamin E, or a component thereof, is present in the formulation at a weight percent of equal to or less than about: 0.1%, 0.5%, 2%, 5%, 7.5%, 10%, 15%, 20%, 25%, 30%, 40%, 60%, or ranges including and/or spanning the aforementioned values. In several embodiments, the vitamin C, or a component thereof, is present in the formulation at a weight percent of equal to or less than about: 0.1%, 0.5%, 2%, 5%, 7.5%, 10%, 15%, 20%, 25%, 30%, 40%, 60%, or ranges including and/or spanning the aforementioned values.

In several embodiments, one or more of the active ingredients of the formulation is botanical and/or is a substance obtained from a plant. In several embodiments, more than one of the active ingredients of the formulation are botanical. In several embodiments, all of the active ingredients of the formulation are botanical. In other embodiments, one or more of the active ingredients of the formulation are not botanical and/or are not derived from plant. In several embodiments, the active ingredients (whether botanical or non-botanical) may be synthetic (e.g., synthesized in a laboratory) or isolated from natural sources (e.g., plants).

In several embodiments, as disclosed elsewhere herein, a first active ingredient is provided in the skin healing formulation. In several embodiments, the first active ingredient is a botanical compound. In several embodiments, the first active ingredient has one or more of analgesic activity, antimicrobial activity, anti-inflammatory activity, and/or antioxidant activity. In several embodiments, the first active ingredient is selected from the group consisting of *Arnica montana* flower extract, bromelain, *calendula officials* flower extract, *Cannabis sativa* seed extract, cannibidiol, *Scutellaria baicalensis* root extract, vitamin E (e.g., tocopherol or tocopheryl acetate), and vitamin C (e.g., l-ascorbic acid, magnesium ascorbyl phosphate, sodium ascorbyl phosphate, ascorbyl glucoside, tetrahexyldecyl ascorbate, 3-o-ethyl ascorbic acid), or combinations of any of the foregoing. In several embodiments, the first active ingredient (or first active ingredients), collectively or individually, are present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values.

In several embodiments, the first active ingredient is *Arnica montana* flower extract. In several embodiments, *Arnica montana* flower extract provides each of analgesic activity, antimicrobial activity, anti-inflammatory activity, and antioxidant activity. In several embodiments, the *Arnica montana* flower extract is present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values.

In several embodiments, the first active ingredient is bromelain. In several embodiments, bromelain provides each of analgesic activity, antimicrobial activity, and anti-inflammatory activity. In several embodiments, bromelain is present in the skin healing formulation (or in the blend formulation) at a weight percent of equal to or less than about: 0.1%, 0.5%, 2%, 5%. 7.5%, 10%, 15%, 20%, 25%, 30%, or ranges including and/or spanning the aforementioned values.

In several embodiments, as disclosed elsewhere herein, a second active ingredient is provided in the skin healing formulation (or in the blend formulation). In several embodiments, the second active ingredient is a botanical compound. In several embodiments, the second active ingredient has one or more of analgesic activity, antimicrobial activity, anti-inflammatory activity, and/or antioxidant activity. In several embodiments, the second active ingredient is selected from the group consisting of bromelain, *Calendula officials* flower extract, *Cannabis sativa* seed extract, cannibidiol, *Scutellaria baicalensis* root extract, vitamin E (e.g., tocopherol or tocopheryl acetate), and vitamin C (e.g., l-ascorbic acid, magnesium ascorbyl phosphate, sodium ascorbyl phosphate, ascorbyl glucoside, tetrahexyldecyl ascorbate, 3-o-ethyl ascorbic acid), or combinations of any of the foregoing. In several embodiments, the second active ingredient (or second active ingredients), collectively or individually, are present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values.

In several embodiments, the second active ingredient is bromelain. In several embodiments, bromelain provides each of analgesic activity, antimicrobial activity, and anti-inflammatory activity. In several embodiments, bromelain is present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values.

In several embodiments, as disclosed elsewhere herein, in addition to a first and second active, one or more additional active agents may be provided in the skin healing formulation (or in the blend formulation). In several embodiments, the one or more additional actives agents may be botanical compounds. In several embodiments, the additional active ingredient(s) has one or more of analgesic activity, antimicrobial activity, anti-inflammatory activity, and/or antioxidant activity. In several embodiments, the additional active ingredient(s) is selected from the group consisting of *Calendula officials* flower extract, *Cannabis sativa* seed extract, cannibidiol, *Scutellaria baicalensis* root extract, vitamin E (e.g., tocopherol or tocopheryl acetate), and vitamin C (e.g., l-ascorbic acid, magnesium ascorbyl phosphate, sodium ascorbyl phosphate, ascorbyl glucoside, tetrahexyldecyl ascorbate, 3-o-ethyl ascorbic acid), or combinations of any of the foregoing. In several embodiments, the additional active agent (or additional active agents), collectively or individually, is present in the skin healing formulation (or in the blend formulation) at a weight percent of equal to or less than about: 0.1%, 0.5%, 2%, 5%, 7.5%, 10%, 15%, 20%, 25%, or ranges including and/or spanning the aforementioned values.

In several embodiments, a recovery accelerator is provided in the skin healing formulation (or in the blend formulation). In several embodiments, the recovery accelerator is a botanical compound. In several embodiments, the recovery accelerator is *Arnica montana* flower extract or bromelain. In several embodiments, the recovery accelerator is *Arnica montana* flower extract. In several embodiments, the recovery accelerator is bromelain. In several embodiments, the recovery accelerator (or recovery accelerators), collectively or individually, are present in the skin healing formulation (or in the blend formulation) at a weight percent of equal to or less than about: 0.1%, 0.5%, 2%, 5%, 7.5%, 10%, 15%, 20%, 25%, 30%, or ranges including and/or spanning the aforementioned values.

In several embodiments, a skin moisturizer is provided in the skin healing formulation (or in the blend formulation). In several embodiments, the skin moisturizer is a botanical compound. In several embodiments, the skin moisturizer is *Arnica montana* flower extract. In several embodiments, the skin moisturizer is selected from the group consisting of hyaluronic acid, a glycol, glycerin, sodium pyrrolidone carboxylic acid, or combinations of any of the foregoing. In several embodiments, the skin moisturizer (or skin moisturizers), collectively or individually, are present in the skin healing formulation (or in the blend formulation) at a weight percent of equal to or less than about: 0.01%, 0.05%, 0.5%, 1%, 5%, 10%, 20%, or ranges including and/or spanning the aforementioned values.

As disclosed elsewhere herein, in several embodiments, the formulation (e.g., skin healing formulation) comprises mixture of different therapeutic agents. In several embodiments, the mixture of therapeutic agents may include one or more analgesics, one or more antimicrobials, one or more anti-inflammatoires, one or more antioxidants, and/or combinations thereof. In several embodiments, the mixture of therapeutic agents comprises, consists essentially of, or consists of *Arnica montana* flower extract. In several embodiments, the mixture of therapeutic agents comprises, consists essentially of, or consists of *Arnica montana* flower extract and bromelain. In several embodiments, the mixture of therapeutic agents comprises, consists essentially of, or consists of *Arnica montana* flower extract, bromelain, *Calendula officials* flower extract, *Cannabis sativa* seed extract, and cannabidiol. In several embodiments, the mixture of therapeutic agents comprises, consists essentially of, or consists of *Arnica montana* flower extract, *Scutellaria baicalensis* root extract, vitamin E (tocopherol and tocopheryl acetate), and vitamin C (l-ascorbic acid, magnesium ascorbyl phosphate, sodium ascorbyl phosphate, ascorbyl glucoside, tetrahexyldecyl ascorbate, 3-o-ethyl ascorbic acid). In several embodiments, the mixture of therapeutic agents comprises, consists essentially of, or consists of *Arnica montana* flower extract, bromelain, *Calendula officials* flower extract, *Cannabis sativa* seed extract, cannabidiol, *Scutellaria baicalensis* root extract, vitamin E (tocopherol and tocopheryl acetate), and vitamin C (l-ascorbic acid, magnesium ascorbyl phosphate, sodium ascorbyl phosphate, ascorbyl glucoside, tetrahexyldecyl ascorbate, 3-o-ethyl ascorbic acid). In several embodiments, the mixture of therapeutic agents comprises, consists essentially of, or consists of *Arnica montana* flower extract, bromelain and a skin moisturizer. In several embodiments, the mixture of therapeutic agents comprises, consists essentially of, or consists of *Arnica montana* flower extract, bromelain, *Calendula officials* flower extract, *Cannabis sativa* seed extract, cannabidiol, and a skin moisturizer. In several embodiments, the mixture of therapeutic agents comprises, consists essentially of, or consists of *Arnica montana* flower extract, *Scutellaria baicalensis* root extract, vitamin E (tocopherol and tocopheryl acetate), vitamin C (l-ascorbic acid, magnesium ascorbyl phosphate, sodium ascorbyl phosphate, ascorbyl glucoside, tetrahexyldecyl ascorbate, 3-o-ethyl ascorbic acid) and a skin moisturizer. In several embodiments, the mixture of therapeutic agents comprises, consists essentially of, or consists of *Arnica montana* flower extract, bromelain, *Calendula officials* flower extract, *Cannabis sativa* seed extract, cannabidiol, *Scutellaria baicalensis* root extract, vitamin E (tocopherol and tocopheryl acetate), vitamin C (l-ascorbic acid, magnesium ascorbyl phosphate, sodium ascorbyl phosphate, ascorbyl glucoside, tetrahexyldecyl ascorbate, 3-o-ethyl ascorbic acid), and a skin moisturizer.

The skin healing formulation 24 can include one or more active ingredients ("actives"), as disclosed elsewhere herein. In several embodiments, as disclosed elsewhere herein, the one or more of the active ingredients are selected form *Arnica*, Bromelain, Vitamin C, and/or Collagen. These ingredients can help reduce bruising and/or swelling of the patient after receiving a lip injection.

At least a portion of the lip mask assembly 10, such as the lip-contacting portion 20, can include at least one adhesive backing, such as an adhesive gel backing. In some embodiments, the entirety of the lip mask assembly 10 includes at least one adhesive backing. The lip-contacting portion 20 and/or the lip mask assembly 10 can include a first adhesive backing and a second adhesive backing. The first and second liners 22 can separate the gel solution filling 26 from the first and second adhesive backings. In some embodiments, the skin healing formulation 24 acts as the first and/or second adhesive backings. For example, the skin healing formulation 24 can be sticky and can help adhere the lip-contacting portion 20 to a user's face. In some embodiments, the lip mask assembly 10 includes other, or additional, formulations, layers, and/or materials to help form the first and/or second adhesive backings and help adhere the lip-contacting portion 20 and/or lip mask assembly 10 to a user's face.

The adhesive backing can initially be covered by a removable protective cover, such as a non-adhesive, fabric covering. In some embodiments, the lip-contacting portion 20 includes at least one protective cover, which can form the plurality of layers of the lip-contacting portion 20. In some embodiments, each side (e.g., surfaces 40, 42) of the lip mask assembly 10 and/or lip-contacting portion 20 includes an adhesive backing (e.g., in some embodiments, the skin healing formulation 24 itself) protected by a removable protective cover (e.g., a first removable protective cover over the first adhesive backing on a first side and a second removable protective cover over the second adhesive backing on a second side, opposite the first side).

In some embodiments, a first protective cover is configured to removably cover skin healing formulation 24 disposed on the surface 40 of the first liner 22. The first protective cover can be configured to be removed to expose skin healing formulation 24 disposed on the surface 40 of the first liner 22. In some embodiments, a second protective cover is configured to removably cover skin healing formulation 24 disposed on the surface 42 of the second liner 22. The second protective cover can be configured to be removed to additionally expose skin healing formulation 24 on the surface 42 of the second liner 22. The surfaces of the protective covers can be continuous (e.g., without openings, perforations, etc.). For example, the protective covers can be configured such that the skin healing formulation 24 positioned beneath the protective covers on the sides of the lip mask assembly 10 (e.g., covered by protective covers removably attached to surfaces 40, 42) does not escape through the protective covers while covered. This can advantageously prevent unintentional use or loss of the skin healing formulation 24 and/or unintentional exposure of the skin healing formulation 24 to the atmosphere prior to use.

The skin healing formulation 24 can be covered by the first and second removable protective covers until the patient desires to apply the formulation 24 to his or her lips. In some embodiments, the patient can remove the first removable protective cover and expose the first adhesive backing (such as, in some embodiments, the skin healing formulation 24 itself) on the first side of the lip-contacting portion 20, apply the first adhesive backing over the patient's mouth and slide the band 12 (including the slits 16 in some embodiments) over the patient's ears to secure the lip mask assembly 10 in position, leave the lip mask assembly 10 on the patient's face for a certain period of time, remove the lip mask assembly 10, and later reuse the lip mask assembly 10 by taking the same steps with respect to the second removable protective cover and the second adhesive backing (e.g., in some embodiments, the skin healing formulation 24 itself) on the second side of the lip-contacting portion 20. For example, in some embodiments, the method for using the lip mask assembly 10 can include applying the lip mask assembly 10 to a user's face such that the skin healing formulation 24 disposed on the surface 40 of the first liner 22 contacts skin of the user and then applying the lip mask assembly 10 to the user's face such that the additional skin healing formulation 24 disposed on the surface 42 of the second liner 22 contacts skin of the user. The method can also include sliding a band 12 (e.g., a support band) over the user's ear to secure the lip mask assembly 10 to the user's face.

The patient can leave the lip mask assembly 10 on his or her face for at least 10 minutes. The patient can leave the lip mask assembly 10 on his or her face for less than 25 minutes. The patient can leave the lip mask assembly 10 on his or her face for about 20 minutes.

In some embodiments, the lip-contacting portion 20 includes an opening 28 for the patient's mouth (FIGS. 1A, 1F, 1G). This can provide for additional breathability. The opening 28 can extend through the plurality of layers of lip-contacting portion 20 to be a through hole or opening through the liners 22 to provide unobstructed airflow through the lip-contacting portion 20 at the opening 28. In some embodiments, the opening 28 can extend through one or more layers of the lip-contacting portion 20 with one or more layers of the lip-contacting portion 20 extending over the area of the opening 28 to provide additional breathability relative to the other layers of the lip-contacting portion.

In some embodiments, the lip-contacting portion 20 is configured to extend over the patient's mouth (FIGS. 2A-2B). As illustrated in FIG. 2A, in some embodiments, the outer periphery of the lip-contacting portion 20 has discrete edges. As illustrated in FIG. 2B, in some embodiments, the outer periphery of the lip-contacting portion 20 is smooth and/or curves continuously.

In some embodiments, the liners 22 comprise a thin film material. In some embodiments, the liners 22 comprise a fabric material. In some embodiments, each of the liners 22 comprises more than one layer of material (e.g., 2 layers, 3 layers, etc.). In some embodiments, the liners 22 comprise recyclable materials. In some embodiments, the liners 22 comprise bioplastic materials, which are biodegradable. For example, in some embodiments the liners 22 comprise starch blends, Polybutylene adipate-co-terephthalate (PBAT), Polybutylene succinate (PBS), Polylactic acid (PLA), and/or Poly-hydroxy-alkanoate (PHA).

The lip mask assembly 10 can be reusable. In some embodiments, the lip mask assembly 10 is configured to be used two or more times. For example, the lip mask assembly 10 can be reversible or double-sided (e.g., each side of the lip mask assembly 10 and/or lip-contacting portion 20 can be configured to be applied to the patient's face). Accordingly, a patient may use the lip mask assembly 10 immediately after a cosmetic treatment (e.g., on the drive home allowing for safe operation of the vehicle with both hands), and then place the lip mask assembly in the freezer or refrigerator after the first use (e.g., after arriving home) to be able to use at a later desired time (e.g., at the home while recovering).

The patient can conveniently attach the lip mask assembly 10 to his or her face after receiving a treatment, while still at the medical office, allowing the patient to receive the healing benefits of icing and/or applying a skin healing formulation 24 (such as a topical analgesic) to his or her lips, hands-free, while driving.

The lip mask assembly 10 can be freezable or otherwise reduced in temperature relative to the environment and/or body temperature of the person or user. The lip mask assembly 10 can be placed in a freezer or refrigerator until the gel solution filling 26 is frozen. Upon returning home from the cosmetic treatment, the patient can remove the lip mask assembly 10 and place it in a freezer for later usage. The patient can reuse the packaging for the lip mask assembly 10. The patient can place the lip mask assembly 10 back into the packaging while not in use, seal the packaging, and place the packaging into a freezer prior to another use.

The lip mask assembly 10 can be disposable. For example, the patient can dispose of the lip mask assembly 10 after usage and/or re-usage. In some embodiments, the lip mask assembly 10 can be recyclable.

Various embodiments and examples of assemblies have been disclosed. Although the assemblies have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above. For example, while disclosed as an embodiment directed to a lip mask assembly 10, the mask assembly can be applied other parts of the face. The lip-contacting portion or cover 20 can be used on any part of the face as a face-contacting portion or cover 20 and can be sized and shaped to fit the desired part of the face. Further, the lip mask assembly 10 can be a body cover or bandage assembly 10 with a body-contacting portion 20 applied to any part of the body. The lip-contacting portion or cover 20 can be used on any part of the body as a body-contacting portion or cover 20 or skin-contacting portion or cover 20 and can be sized and shaped to fit the desired part of the body. In some embodiments, the band 12 can be a stretchable bandage material with Velcro for wrapping around a body part, such as a limb. In some embodiments, where the body cover assembly 10 is used without a band 12, the body cover assembly can be adhered to the body part as discussed herein, taped using medical tape, and/or otherwise secured to any desired body part using for example gauze.

What is claimed is:

1. A lip mask assembly for placement over lips of a user to facilitate skin healing of the user, comprising:
    a support band comprising a first portion and a second portion, wherein each of the first and second portions of the support band is configured to receive an ear of a user;
    a lip-contacting portion configured to contact lips of the user, the lip-contacting portion attached to the support band and positioned between the first and second portions of the support band, the lip-contacting portion comprising:
        a first liner having an outwardly facing surface and an inwardly facing surface;
        a second liner having an outwardly facing surface and an inwardly facing surface, the inwardly facing surface of the second liner positioned to face the inwardly facing surface of the first liner; and
        a gel solution filling disposed between the inwardly facing surface of the first liner and the inwardly facing surface of the second liner, the gel solution filling configured to be cooled relative to ambient temperature;
    a skin healing formulation disposed on the outwardly facing surface of the first liner and the outwardly facing surface of the second liner, the skin healing formulation comprising at least a first active botanical compound and at least a second active botanical compound,
    a first protective cover configured to removably cover the skin healing formulation disposed on the outwardly facing surface of the first liner, the first protective cover configured to be removed to expose the skin healing formulation; and
    a second protective cover configured to removably cover the skin healing formulation disposed on the outwardly facing surface of the second liner, the second protective cover configured to be removed to expose the skin healing formulation.

2. The lip mask assembly of claim 1, further comprising a seal between the first and second liners, wherein the seal is configured to prevent leakage of the gel solution filling from the lip-contacting portion.

3. The lip mask assembly of claim 1, wherein the lip-contacting portion further comprises an opening for the user's mouth, the opening extending through the first and second liners.

4. The lip mask assembly of claim 1, wherein the lip mask assembly comprises adhesive configured to support the lip mask assembly on the user's face.

5. The lip mask assembly of claim 1, wherein the gel solution filling is configured to be frozen.

6. The lip mask assembly of claim 1, wherein the support band comprises a stretchy fabric, each of the first and second portions of the support band comprising a slit for receiving one of the user's ears.

7. The lip mask assembly of claim 1, wherein the first active botanical compound is configured to provide analgesic activity.

8. The lip mask assembly of claim 1, wherein the first active botanical compound is configured to provide antimicrobial activity.

9. The lip mask assembly of claim 1, wherein the first active botanical compound is configured to provide anti-inflammatory activity.

10. The lip mask assembly of claim 1, wherein the first active botanical compound is configured to provide antioxidant activity.

11. The lip mask assembly of claim 1, wherein the first active botanical compound is an *Arnica montana* extract.

12. The lip mask assembly of claim 1, wherein the second active botanical compound is configured to provide analgesic activity.

13. The lip mask assembly of claim 12, the second active botanical compound is selected from the group consisting of bromelain, *Calendula officials* flower extract, *Cannabis sativa* seed extract, cannabidiol, *Scutellaria baicalensis* root extract, tocopherol, tocopheryl acetate, ascorbic acid, magnesium ascorbyl phosphate, sodium ascorbyl phosphate, ascorbyl glucoside, tetrahexyldecyl ascorbate, and 3-o-ethyl ascorbic acid.

14. The lip mask assembly of claim 1, wherein the skin healing formulation comprises a skin moisturizer, wherein the skin moisturizer comprises hyaluronic acid, a glycol, glycerin, sodium pyrrolidone carboxylic acid, or combinations of any of the foregoing.

15. A method of using a lip mask assembly, comprising:
    removing a first protective cover from a surface of a first liner of a lip-contacting portion of the lip mask assembly to expose a skin healing formulation disposed on the surface of the first liner, wherein the skin healing formulation comprises at least a first active botanical compound and at least a second active botanical compound;
    removing a second protective cover from a surface of a second liner of the lip-contacting portion of the lip mask assembly to expose additional skin healing formulation disposed on the second surface of the second liner;
    applying the lip mask assembly to a user's face such that the skin healing formulation disposed on the surface of the first liner contacts skin of the user and such that the additional skin healing formulation disposed on the surface of the second liner contacts skin of the user; and
    sliding a support band over the user's ear to secure the lip mask assembly to the user's face.

16. The method of claim 15, further comprising cooling a gel solution filling in contact with the first liner to a temperature below ambient temperature to provide cooling to skin of the user after applying the lip mask assembly to the user's face.

* * * * *